(12) United States Patent
Meyer

(10) Patent No.: US 9,196,046 B2
(45) Date of Patent: Nov. 24, 2015

(54) MEDICAL IMAGING

(75) Inventor: Carsten Meyer, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 974 days.

(21) Appl. No.: 13/260,679

(22) PCT Filed: Mar. 18, 2010

(86) PCT No.: PCT/IB2010/051179
§ 371 (c)(1),
(2), (4) Date: Dec. 6, 2011

(87) PCT Pub. No.: WO2010/109384
PCT Pub. Date: Sep. 30, 2010

(65) Prior Publication Data
US 2012/0087558 A1   Apr. 12, 2012

(30) Foreign Application Priority Data

Mar. 27, 2009 (EP) .................................... 09156380

(51) Int. Cl.
*G06T 7/00* (2006.01)
*A61B 8/00* (2006.01)
(Continued)

(52) U.S. Cl.
CPC ............... *G06T 7/0081* (2013.01); *A61B 8/42* (2013.01); *A61B 8/488* (2013.01); *G06T 3/0068* (2013.01);
(Continued)

(58) Field of Classification Search
CPC ... G06T 3/0068; G06T 7/0079; G06T 7/0081; G06T 2207/10132; G06T 2207/10136; G06T 2207/20112; G06T 2207/30004; G06T 7/0089; G06T 7/20; A61B 8/42; A61B 8/488
See application file for complete search history.

(56) References Cited

U.S. PATENT DOCUMENTS 5,825,908 A  * 10/1998 Pieper et al. ................... 382/131
5,926,568 A  *  7/1999 Chaney et al. ................. 382/217
(Continued)

FOREIGN PATENT DOCUMENTS

JP    2007282945 A    1/2007
WO   2004081875 A2   9/2004
(Continued)

OTHER PUBLICATIONS

By Marius George Linguraru et al.; Entitled: Real-Time Tracking and Shape Analysis of Atrial Septal DEFE4CTS in 3D Echocardiography; Miccai Original Investigations; Academic Radiology, vol. 14, No. 11, Nov. 2007; pp. 1298-1309.
(Continued)

*Primary Examiner* — Manav Seth

(57) ABSTRACT

Ultrasound imaging, or ultrasonography, is a convenient imaging modality for diagnostic purposes. During procedures requiring visualization, the user coordinates the movement of the transducer through the manual selection of an appropriate representation on the screen. Ultrasound may also be employed for functional measurements. Typically, the measurement requires the manual selection of target planes, lines, or volumes where the measurement is to be performed. Therapeutic applications of ultrasound are also known in the art. Such applications typically employ higher energies, and therefore inaccuracies in positioning may result in damage to surrounding tissues. The invention provides a system and method for repeated determination of a first vector between a reference structure comprised in an anatomical volume and a medical imaging transducer configured to provide imaging data of the anatomical volume. The invention provides an automated tracking system of the reference structure, requiring that the user only selects the reference structure.

15 Claims, 5 Drawing Sheets

(51) Int. Cl.
  *G06T 3/00* (2006.01)
  *A61B 8/08* (2006.01)
  *G06T 7/20* (2006.01)
  *G01S 7/52* (2006.01)

(52) U.S. Cl.
  CPC ............... *G06T 7/0089* (2013.01); *G06T 7/20* (2013.01); *A61B 8/4245* (2013.01); *G01S 7/52063* (2013.01); *G01S 7/52073* (2013.01); *G06T 2207/10132* (2013.01); *G06T 2207/20092* (2013.01); *G06T 2207/20112* (2013.01)

(56) References Cited

U.S. PATENT DOCUMENTS

| | | | |
|---|---|---|---|
| 6,144,386 A * | 11/2000 | Pratt | 715/848 |
| 6,342,889 B1 | 1/2002 | Callahan | |
| 6,501,848 B1 * | 12/2002 | Carroll et al. | 382/128 |
| 6,751,340 B2 * | 6/2004 | Prokoski | 382/118 |
| 6,837,892 B2 * | 1/2005 | Shoham | 606/130 |
| 6,842,638 B1 * | 1/2005 | Suri et al. | 600/425 |
| 6,907,281 B2 * | 6/2005 | Grzeszczuk | 600/407 |
| 6,950,544 B2 * | 9/2005 | Ashton | 382/131 |
| 7,170,533 B2 | 1/2007 | Launay et al. | |
| 7,231,076 B2 * | 6/2007 | Fu et al. | 382/131 |
| 7,257,237 B1 * | 8/2007 | Luck et al. | 382/103 |
| 7,457,439 B1 * | 11/2008 | Madsen et al. | 382/107 |
| 7,512,255 B2 * | 3/2009 | Kakadiaris et al. | 382/118 |
| 7,720,276 B1 * | 5/2010 | Korobkin | 382/154 |
| 7,787,676 B2 | 8/2010 | Drobnitzky | |
| 7,831,076 B2 * | 11/2010 | Altmann et al. | 382/128 |
| 7,930,014 B2 * | 4/2011 | Huennekens et al. | 600/407 |
| 8,556,815 B2 * | 10/2013 | Pelissier et al. | 600/443 |
| 8,698,795 B2 * | 4/2014 | Grewer et al. | 345/419 |
| 2002/0028006 A1 | 3/2002 | Novak et al. | |
| 2004/0092815 A1 * | 5/2004 | Schweikard et al. | 600/425 |
| 2004/0228453 A1 * | 11/2004 | Dobbs et al. | 378/210 |
| 2005/0096543 A1 * | 5/2005 | Jackson et al. | 600/441 |
| 2005/0240882 A1 | 10/2005 | Morita et al. | |
| 2008/0015428 A1 | 1/2008 | Epstein et al. | |
| 2010/0246911 A1 * | 9/2010 | Rabben et al. | 382/131 |

FOREIGN PATENT DOCUMENTS

| | | |
|---|---|---|
| WO | 2005067800 A1 | 7/2005 |
| WO | 2005101277 A2 | 10/2005 |
| WO | 2008110013 A1 | 9/2008 |

OTHER PUBLICATIONS

By Olivier Ecabert et al.; Entitled: Automatic Model-Based Segmentation of the Heart in CT Images; IEEE Transactions on Medical Imaging, vol. 27, No. 9. Sep. 2008; pp. 1189-1201.

By Michael R. Kaus, PhD et al.; Automated Segmentation of MR Images of Brain Tumors; vol. 218, No. 2; Radiology; Feb. 2001. pp. 586-591.

Fan, L. et al. "Evaluation and application of 3D lung warping and registration model using HRCT images", Proc. SPIE 4321, Medical Imaging 2001: Physiology and Function from Multidimensional Images, 234 (May 21, 2001).

* cited by examiner

MEDICAL IMAGING

FIELD OF THE INVENTION

The invention relates to a system and method for providing imaging data of a reference structure in an anatomical volume.

BACKGROUND OF THE INVENTION

Ultrasound imaging, or ultrasonography, is a convenient imaging modality for diagnostic purposes. It may be employed before, during or after a therapeutic intervention. Typically, a healthcare professional uses a hand-held probe, or transducer, which is moved as appropriate to visualize reference structures. In many cases, the transducer is placed on the surface of the body. However, in some specialized procedures, such as endovaginal, endorectal and transesophageal procedures, specific transducers are placed inside the patient's body. Small transducers may even be mounted on catheters and inserted into blood vessels to image the vessel walls.

Recent advances in ultrasound require real-time monitoring in an increasing range of diagnostic and interventional procedures. For example, for the diagnosis and treatment of an atrial septal defect (ASD) or a patent foramen ovale (PFO), the healthcare professional may employ:

Transesophageal Echocardiography (TEE), where the ultrasound transducer is placed inside the esophagus Transthoracic Echocardiography (TTE), where the ultrasound transducer is placed on the chest, outside the body.

Intracardiac Echo (ICE), where the ultrasound transducer is placed in the venous system and advanced to the heart.

During procedures requiring visualization, the user coordinates the movement of the transducer by the manual selection of an appropriate representation on the screen, such as a 2-D viewing cross-section of the 3-D imaging volume. In systems of the prior art, such as disclosed in U.S. Pat. No. 6,342,889, a system is provided that provides an initial view, the user then selects points of interest, and the system provides a representation including the selected points on a display. Although a degree of automation is provided, the operator of the system is required to frequently input the points of interest. While this may be acceptable in off-line applications where the user is processing previously acquired imaging data, it is not acceptable in real-time applications, where the input of the user directly affects the accuracy and reliability of the procedure being performed. Users will be required to make choices and make viewing selections throughout the procedure, and even highly trained operators will often be required to perform trial-and-error to obtain the desired results.

Ultrasound may also be employed for functional measurements, such as Doppler measurements, where the Doppler effect is exploited to measure the direction and speed of movement of a reference structure, for example a portion of a heart valve or a jet of blood flow in a vessel, relative to the transducer. Typically, the measurement requires the manual selection of target planes, lines, or volumes where the measurement is to be performed.

Doppler measurements may be performed using both continuous and pulsed systems, with pulsed systems having the advantage that distance information about the depth or range of the reference structure may be obtained from the ultrasound pulses.

However, pulsed Doppler is known to suffer from aliasing if the velocity of the reference structure and the angle between the measurement beam and the blood flow direction combine to give a Doppler frequency greater than half of the pulse repetition frequency. This creates ambiguity in the Doppler signal, and may cause misinterpretation of the reference object's movement. Typically low velocities, for example venous flow, are measured using low pulse repetition frequencies, and high velocities, for example arterial flow, are measured using higher pulse repetition frequencies.

An additional problem of pulsed Doppler is that the depth of measurement is limited by the pulse repetition frequency chosen, because the time interval must be sufficient to allow a pulse to travel from the transducer to the reference structure and back, before the next pulse is emitted.

Systems are known in the prior art which combine the visualization and functional possibilities. This may be done using different transducers, or more commonly a single transducer which can operate in two different modes, for example pulsed Doppler for the functional mode and B-mode imaging for the visualization.

In Color Doppler ultrasound, the Doppler shifts in a few thousand sample volumes in an image plane are measured. For each sample volume, the average Doppler shift is encoded as a color, and displayed on top of the B-mode image. Again the transducer is switched between two different modes of operation.

The measurement of samples and the processing of the results require considerable computational power, making such an instrument expensive.

Furthermore, functional measurements in general require the ultrasound device to be configured appropriately in terms of transducer orientation, selection of measurement volume, selection of the pulse repetition frequency etc., so that the ultrasound beam is reflected precisely at the selected reference structure. The position and extent of the measurement volume is conventionally selected by the user, and therefore can result in inaccuracies in the results measured.

In some cases, ultrasound may be employed during an intervention using a surgical instrument, for example a catheter in the treatment of an atrial septal defect (ASD) or a patent foramen ovale (PFO).

PCT application WO 2005/101277 discloses a system that provides in real-time three-dimensional imaging for use during an intervention with a biopsy needle. This system segments the biopsy needle from the volume, using a Hough Transform to give the position and elongation of the needle. This may then be used to automatically select image slices, such that the user always looks in the direction of the biopsy needle.

Although acceptable for some applications, this system can only provide a limited field of view from the viewpoint of the biopsy needle, making it very easy for the user to navigate the needle incorrectly and to lose orientation. The user must then manually select image planes to regain the orientation, or even move the needle back until orientation is restored.

Therapeutic applications of ultrasound are also known in the art. They provide localized heating and/or mechanical agitation in anatomical structures. For example, Focused Ultrasound Surgery (FUS) or High-Intensity Focused Ultrasound (HIFU) may be used to heat-up reference structures such as cysts and tumors. In another example, lithotripsy employs ultrasound to break up reference structures such as stones in the kidney, bladder, ureter or gall bladder. Such applications typically employ higher energies than for visualization or functional measurement, and therefore inaccuracies in positioning may result in damage to surrounding tissues. In the art it is known for the user to determine the position using a modality suitable for visualization, such as MRI.

SUMMARY OF THE INVENTION

It is an object of the invention to provide a system and method for providing imaging data of a reference structure in an anatomical volume.

The invention is defined by the independent claims. Advantageous embodiments are defined in the dependent claims.

According to a first aspect of the invention, a system is provided for repeated determination of a first vector between a reference structure comprised in an anatomical volume and a medical imaging transducer configured to provide imaging data of the anatomical volume; the system comprising:
- a user input configured to specify the reference structure;
- an imager configured to receive the imaging data;
- a model input configured to provide a model of the reference structure;
- a segmenter configured to receive the model and to segment the imaging data using the model, whereby the imaging data associated with the reference structure is at least partially annotated, and
- a determiner configured to receive the annotated imaging data of the reference structure and to determine the first vector between the transducer and the reference structure, based on the annotated imaging data.

The invention is based upon the insight that many of the manual actions required from a user are the result of his trying to keep the orientation of the transducer to the reference structure within certain limits, and that the user moves the transducer to compensate for anatomical differences in patients, for both static and moving reference structures. A high degree of training is therefore required to be able to interpret the imaging data and to be able to make the appropriate selection.

The orientation is even more critical for functional measurements. The position and extent of a position of measurement is selected by the user, and therefore manual selection can lead to inaccuracies in the results measured. For example, in Doppler measurement, the accurate quantification of blood flow requires knowledge of the Doppler angle (between the ultrasound beam and the direction of blood flow). A high degree of training is therefore required to be able to interpret the ultrasound data and to be able to select the appropriate measurement lines, volumes or planes.

For therapeutic applications, an incorrect orientation may damage adjacent tissues, so the orientation between the transducer and the reference structure benefits from a high-degree of accuracy.

The ultrasound user wishes to perform the procedure during a period of time, without having to manually correct the relevant settings to compensate for movements of the transducer and/or the reference structure. The invention provides an automated tracking system of the reference structure, requiring that the user only selects the reference structure. This reference structure is then tracked by means of the repeatedly applied patient-specific segmentation, and the result of the segmentation is used to automatically update relevant parameters, such as the views for visualization or values for functional measurements and therapeutic procedures. The accuracy and relative speed with which this may be performed using patient-specific data makes the invention particularly useful for on-line measurements, where the actions and selections of a user may greatly influence the accuracy and reliability of measurement results or even the effect of therapy.

Additionally, in functional measurements and therapeutic applications, the user may be required to specify a distance. For example, in Doppler pulse wave blood flow the distance between the transducer and the reference structure may be required to determine the recommended pulse-repetition frequency range. Typically, the user would have to estimate this based upon average values for comparable patients, or by performing a separate measurement. Inaccuracies in such a value affect the accuracy of the functional values, and in the case of therapeutic application, can damage adjacent tissues.

The invention utilizes a patient-specific model to provide such values, reducing the problems associated with inaccuracies. Additionally, the risks of the user making a mistake by choosing the wrong reference structure are also reduced—for example, it may be difficult to identify from visualization data a particular blood vessel, but by applying a model, the correlation may be quantified and provided to the user as appropriate feedback.

According to a further aspect of the invention, the system is configured so that the determiner is further configured to monitor a geometric parameter selected from the group consisting of: the length of the first vector, the direction of the first vector, the proximity of the reference structure to a boundary of the anatomical volume, the proportion of the reference structure within the anatomical volume, a geometric quantity of the reference structure, or any combination thereof; the determiner being further configured to alert the user if the geometric parameter deviates from a predetermined value or range of values.

Values derived by the system may be used to alert the user automatically. For example, if a heart valve is selected as the reference structure to be tracked during the procedure, and it starts to move out of the anatomical volume where imaging data is being produced by the transducer, the user may benefit from a warning that the position of the transducer and/or the patient may need to be changed.

During functional measurement or therapeutic applications, a monitoring of the orientation of the reference structure to the transducer may be used to alert the user if these values have deviated, or are about to deviate, from a predetermined value or a predetermined range of values. Orientation may be quantified as a vector, with a length and a relative direction. For functional measurements, this reduces the risk of an incorrect measurement, and for therapeutic applications this reduces the risk of damage to adjacent tissues. For example, the user may be alerted to potentially ambiguous measurements because the reference structure is too far from an ultrasound transducer.

According to another aspect of the invention, the determiner is further configured to determine from the annotated data a viewing cross-section based upon the first vector, wherein the viewing cross-section intersects the reference structure and the system further comprises a display configured to provide a representation of the viewing cross-section.

For example, the positions of organs may differ from patient to patient, and the degree of movement of a heart valve may also vary. Using the invention, the user selects the heart valve as the reference structure, and after the model is applied to annotate the image data, the position of the heart valve is tracked from the imaging data. The system then determines an appropriate 2D cross-section, for example from a set of landmarks specified within the model for the heart valve. The appropriate representation of the 2D cross-section is then displayed. By repeatedly updating the segmentation, the position of the heart valve may be tracked, and the representation of the 2D cross-section updated in a corresponding way.

According to another aspect of the invention, the determiner is further configured to determine a functional parameter, based upon the segmented data of the reference structure.

The accuracy of functional measurements may be improved by determining anatomical distances from the segmented data, which has been adapted to the patient-specific anatomy. Again, providing the values from patient-specific data is more accurate than values that the user must estimate from average patient details or imaging data. For example, the user may be alerted to potentially ambiguous measurements because the angle between the ultrasound beam and the blood flow direction, required for the calculation using the Doppler effect, has deviated from a predetermined value or a predetermined range of values.

In another aspect of the invention, the system further comprises a tracker configured to determine the position of a surgical instrument in the anatomical volume, and the determiner is further configured to determine a second vector between the reference structure and the surgical instrument.

When using the systems and methods of the prior art during an intervention, the user needs to frequently change view planes manually if the orientation is lost. This can happen if the user is concentrating on following the path of the catheter into the patient—he may inadvertently move the transducer such that the reference structure moves out of range.

As the reference structure is the structure towards which the catheter is being moved, the user generally prefers to keep this structure within range at all times during the procedure. By using the invention, the position of the instrument may be determined, and its position within the patient-specific anatomical model may be accurately and repeatedly determined relative to the reference structure.

In another aspect of the invention, the determiner is further configured to monitor a geometric parameter selected from the group consisting of the length of the second vector, the direction of the second vector, the proximity of the surgical instrument to a boundary of the anatomical volume, the proportion of the surgical instrument within the anatomical volume, a geometric quantity of the instrument, or any combination thereof; the determiner being further configured to alert the user if the geometric parameter deviates from a predetermined value or range of values.

By combining the position of the instrument with the values which may be determined using the patient-specific annotated data, the relative position of the instrument may be determined with a high-degree of accuracy. In a procedure where the instrument is being moved by hand to the reference structure, it may be advantageous to alert the user if the instrument is outside, or at the edge of, the anatomical volume. Additionally, the distance between the instrument and the reference structure gives valuable feedback to the user on how far the instrument still needs to be moved.

In another aspect of the invention, the tracker is comprised in the segmenter, and further configured to segment the imaging data, whereby the imaging data associated with the surgical instrument is at least partially annotated.

If sufficient computational power is available, the tracking system for the instrument may be implemented using model-based segmentation. By choosing not to employ a separate tracking system, a simplification of the system and of the operation by the user may be achieved.

In still another aspect of the invention, the system further comprises an instrument detector configured to detect the surgical instrument, and the tracker is configured to determine the position of the surgical instrument in the anatomical volume, based upon signals from the instrument detector.

Any suitable instrument tracking system known in the art may be employed, allowing the position of the instrument within the patient-specific anatomical model to be accurately and repeatedly determined. It is therefore not required to employ computationally intensive algorithms to determine the instrument position.

In a further aspect of the invention, the determiner is further configured to determine from the annotated data a viewing cross-section based upon the first and second vector, wherein the viewing cross-section intersects the reference structure and the surgical instrument, and the system further comprises a display configured to provide a representation of the viewing cross-section.

As the position of both the reference structure and the instrument are accurately known, appropriate values may be used to provide an automatic or highly-automated selection of a new viewplane to visualize both the reference structure and the instrument.

In the example of instrument tracking using a non-segmentation technique, the "world coordinates" of the instrument may be obtained in real-time. By frequently applying segmentation using the model, the position of the reference structure, for example, the atrial septal wall, can be tracked and—using an appropriate calibration—expressed in "world coordinates". From this information, an optimal viewplane may be calculated containing the instrument position and appropriate points on the reference structure, and continuously updated on the display to track the position of the instrument in relation to the reference structure.

In another aspect of the invention, a method is provided for repeated determination of a first vector between a reference structure comprised in an anatomical volume and a medical imaging transducer configured to provide imaging data of the anatomical volume;

the method comprising:
a user specifying the reference structure;
providing a model of the reference structure;
segmenting the imaging data using the model, whereby the imaging data associated with the reference structure is at least partially annotated, and
determining the first vector between the transducer and the reference structure, based on the annotated imaging data of the reference structure.

It will be appreciated by those skilled in the art that two or more of the above-mentioned embodiments, implementations, and/or aspects of the invention may be combined in any way deemed useful.

Modifications and variations of the image acquisition apparatus, of the workstation, of the system, and/or of the computer program product, which correspond to the described modifications and variations of the method, can be carried out by a person skilled in the art on the basis of the present description.

It will also be obvious to the skilled person that the invention does not need to be limited to the ultrasound modality. It may be used with any imaging modality where it is necessary to provide updated selections to compensate for movements of the measurement device, anatomical movements of the patient, anatomical movements of the reference structure, or any combination thereof.

BRIEF DESCRIPTION OF THE DRAWINGS

These and other aspects of the invention are apparent from and will be elucidated with reference to the embodiments described hereinafter.

In the drawings.

The Figures are purely diagrammatic and not drawn to scale. Particularly for clarity, some dimensions are exaggerated strongly. Similar components in the Figures are denoted by the same reference numerals as much as possible.

DETAILED DESCRIPTION OF THE PREFERRED EMBODIMENTS

Figure 1:
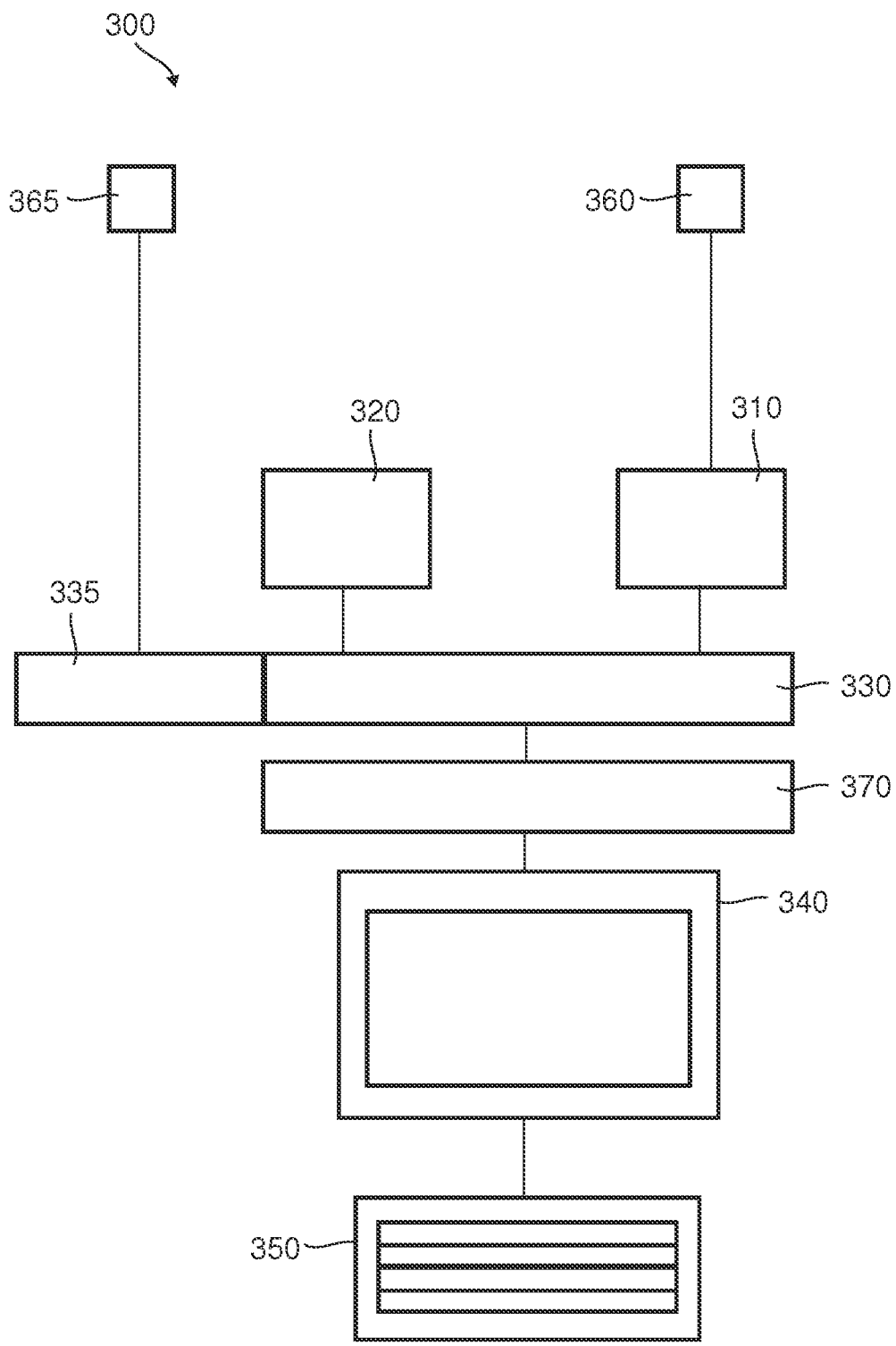
FIG. 1 shows the system according to the invention.

A system 300 for providing imaging data of a specific anatomical volume is depicted in FIG. 1. The system 300 comprises:

- a medical imaging transducer 360 configured to provide imaging data of an anatomical volume 100. For example, this is an ultrasound transducer, suitable for visualization, for functional measurements, or for therapeutic applications. In practice, the anatomical volume may be considered to be the anatomical region of a patient within the range of the imaging transducer 360;
- a user input 350 configured to specify a reference structure 120 in the anatomical volume. Typically, the user input 350 provides for interaction with the system in any form known in the art, for example, as icons, thumbnails, menus, and pull-down menus. The user input 350 may also comprise a keyboard, mouse, trackball, pointer, drawing tablet or the like;
- an imager 310 configured to receive the imaging data. The imager 310 cooperates with the transducer 360 to provide the imaging data in an appropriate format to the segmenter 330. The configuration of the imager 310 is therefore dependent upon the imaging modality employed by the transducer 360 and the operating mode of transducer 360. In practice, the imager 310 may even be physically integrated with the transducer 360, allowing interchangeability;
- a model input 320 configured to provide a generic model corresponding to the reference structure 120. This model may be provided by appropriate segmentation of the imaging data. However, by utilizing registration and overlay techniques known in the art, the model may be based upon imaging data from other modalities, such as X-ray Imaging, Computed Tomography (CT), Magnetic Resonance Imaging (MRI), Positron Emission Tomography (PET), Single Photon Emission Computed Tomography (SPECT) and Nuclear Medicine (NM);
- a segmenter 330 configured to receive the model and to segment the imaging data using the model, whereby the imaging data associated with the reference structure 120 is at least partially annotated, and
- a determiner 370 configured to receive the annotated imaging data of the reference structure 120 and to determine the first vector between the transducer 360 and the reference structure 120, based on the annotated imaging data.

The system is further configured for the repeated determination of a first vector between the reference structure 120 and the medical imaging transducer 360.

Figure 4:
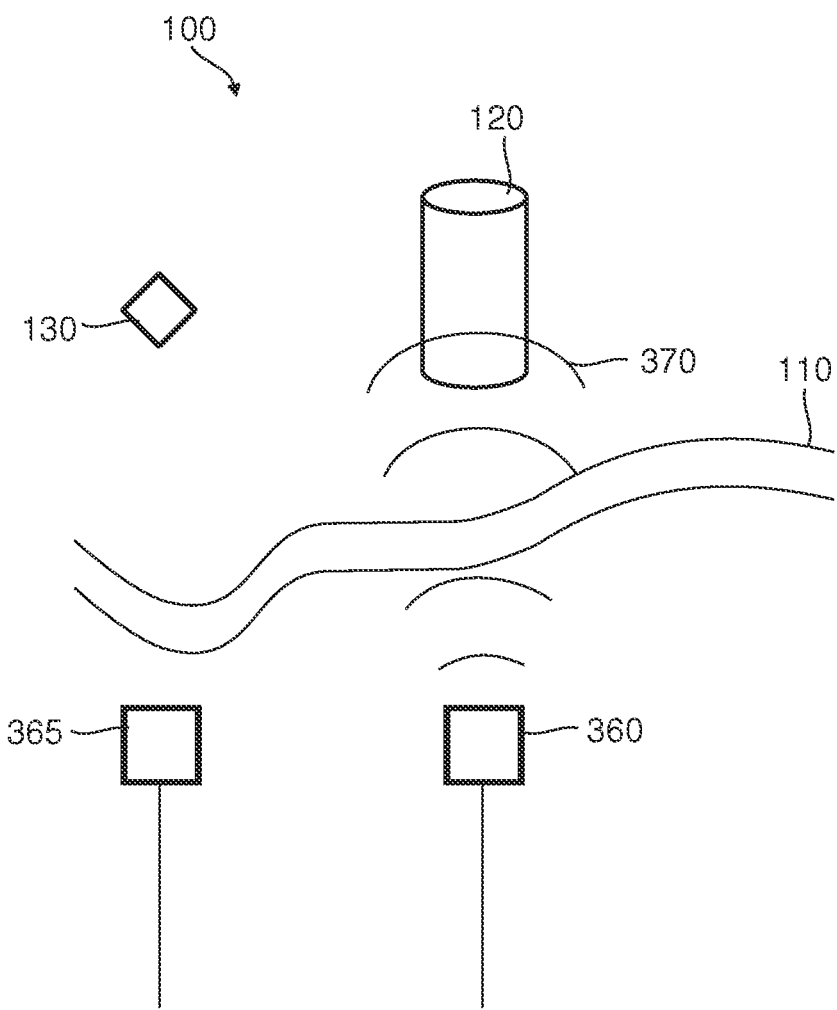
FIG. 4 depicts schematically the positioning of the transducers relative to the reference structure and a surgical instrument.

FIG. 4 depicts the schematic relationship between the transducer 360 and the anatomical volume 100, which comprises a reference structure 120. The transducer 360 is positioned such that it can provide imaging data of the anatomical volume 100, by either solely detecting a property or phenomenon or emitting an appropriate energy 370 and detecting a property or phenomenon triggered by that energy 370. Typically, the anatomical volume 100 will be bounded by an anatomical surface 110, such as the skin. However, this need not always be the case as transducers 360 may also be inserted into a patient's body.

The phrase "imaging data" should be interpreted broadly as data acquired using an imaging technique. It does not imply that the data is only suitable for providing a visualization, or visual image, of the data.

The phrase "anatomical volume" should be interpreted broadly as any region comprising anatomy. It may comprise or even consist of one or more reference structures.

The phrase "reference structure" should also be interpreted broadly. For example, a reference structure may be an organ, a part of an organ, a lobe of an organ, a skeletal bone, a part of a skeletal bone, a muscle, a part of a muscle, a lymph node, part of a lymph node, a vessel, and part of a vessel. Such a structure may also include a tumor, a primary tumor, a metastatic tumor, a cyst, a pseudocyst, a neoplasm, a lymph node, a lymphoma fibroid, and a nevus.

Additionally, the reference structure may be a region of bodily fluid, such as blood flowing through a section of a blood vessel. This is typically the case when functional measurements, such as blood velocity, are made.

The reference structure may even be stones in the kidney, bladder, ureter or gall bladder.

During use, the user will have a reference structure 120 in mind, and will place the transducer 360 in an appropriate position to collect imaging data of the reference structure 120. Typically, imaging data will be collected from a volume larger than that of the reference structure 120, namely the anatomical volume 100.

The user interacts with the system, using the user input 350 to select the reference structure 120. This selection determines the anatomical object to be tracked, and determines the appropriate model to be used for segmentation. Typically, a database of appropriate models will be made available to the user for different procedures and applications.

The segmenter 330 applies the model to the imaging data, thereby annotating the imaging data corresponding to the reference structure 120 as imaged in the patient.

The determiner 370 determines the orientation of any characteristic point of the reference structure 120 to the transducer 360. One of these two points is selected as the origin of a first vector to the other point—it is not important which one is used, but it may be advantageous to use the reference structure 120 as the origin. This vector will have a length and directional components. Any convenient coordinate system may be used, such as Euclidean or polar.

The system then updates the imaging data, repeats the segmentation and repeats the determination of the first vector.

Alternatively, the user may select a reference structure 120 initially, and the determiner 370 may be further configured to provide assistance as to where to place the transducer 360.

Figure 2:
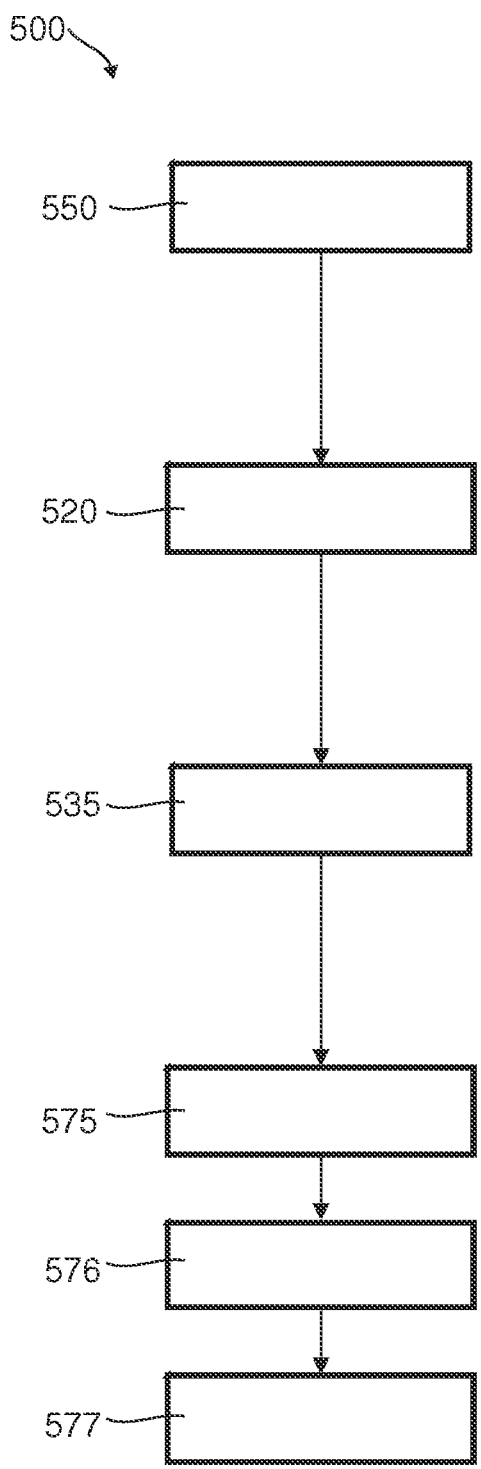
FIG. 2 depicts the method according to the invention.

The system is configured for performing the method 500 according to the invention, which is depicted in FIG. 2. The method 500 comprises:

- providing a medical imaging transducer 360 configured to provide imaging data of an anatomical volume 100;
- specifying 550, by a user, a reference structure 120 in the anatomical volume 100. The user is in effect selecting an anatomical reference point, the position of which is to be tracked during the measurement;
- providing 520 a model of the reference structure 120;

segmenting 535 the imaging data using the model, whereby the imaging data associated with the reference structure 120 is at least partially annotated. Segmentation of the imaging data may be simpler if the model is derived from the same modality as the imaging data; and determining 575 the first vector between the transducer 360 and the reference structure 120, based on the annotated imaging data of the reference structure 120.

The method further comprises the repeated determination of the first vector between the reference structure 120 and the transducer 360.

The accuracy provided by the invention is based upon the accurate and robust representation of anatomy, in particular organ anatomy, which may be achieved using model-based segmentation, even in the presence of image artifacts and noise. Any appropriate model-based segmentation known in the art may be used. For example, see O. Ecabert, J. Peters, H. Schramm et al., "Automatic model-based segmentation of the heart in CT images", IEEE Trans. Med. Im., in press.

It may be advantageous to reduce the computational power required to perform the real-time segmentation and determination. This may be achieved by any suitable technique known to the skilled person, such as minimizing the anatomical volume, varying the resolution dependent on the distance from the reference structure, minimizing the size of the reference structure, reducing the frame rate, or reducing the number of vertices in the model.

Although the method 500 may be performed completely automatically, it is also envisioned that the method 500 may be implemented such that the healthcare professional operating the invention is prompted to make a selection from a limited number of choices. In other words, the method is highly-automated. This may also reduce the computational power required. For example, at suitable points during the measurement, a pull-down menu may be presented or the professional may be prompted to select one of several alternatives annotated on a display of the imaging data. An intermediate embodiment is also envisioned, where sections of the measurement are performed automatically, punctuated by infrequent manual selections.

The implementation may be further simplified by tracking the position of the transducer in any appropriate manner known in the art.

It may be advantageous to further configure the determiner 370 to monitor a geometric parameter, and to alert the user if the geometric parameter deviates from a predetermined value or range of values. For example, the orientation of the transducer 360 to the reference structure 120 may be expressed as a vector, having a length and a direction. Either one or both of these parameters may be monitored to warn the user that the procedure may be less effective, or even dangerous, due to an incorrect positioning.

Other suitable parameters include the proximity of the reference structure 120 to a boundary of the anatomical volume 100, the proportion of the reference structure 120 within the anatomical volume 100, or any combination thereof;

The parameter may even be a geometric quantity of the reference structure 120, as geometry is available from the patient-specific segmented data.

For functional measurement procedures, the determiner 370 may be further configured to determine a functional parameter, based upon the segmented data of the reference structure 120.

For example, for monitoring the diameter of the pulmonary vein ostia, an appropriate elliptical cross-section of the individual ostia may be comprised in the model. By adapting the generic model to the imaging data, a patient-specific characterization of the pulmonary vein ostia is obtained, and the geometrical parameters of the ellipse may be determined by the determiner 370. These patient-specific pulmonary vein ostia diameters are then directly determined.

It will be apparent to the skilled person that the system and method according to the invention may be applied to functional measurements only, providing improvement in positional accuracy and therefore also in the accuracy of the functional measurement. However, in practice, the user will require a way of locating the reference structure 120 in the anatomical volume 100. This may be provided by a separate visualization modality and some form of co-ordinate conversion to align the visualization and functional modality. This may alternatively or additionally be provided by using a functional measurement modality to provide visualization data— for example, a pulsed Doppler ultrasound system may be switched between a visualization mode and a functional measurement mode.

For procedures requiring visualization, either individually or in combination with functional measurements or therapeutic procedures, the determiner 370 may be further configured to determine from the annotated imaging data a viewing cross-section based upon the orientation of the reference structure 120 to the transducer 360. This is preferably a 2D viewing cross-section which intersects the reference structure 120. By providing the system with a display 340, a representation of the 2D viewing cross-section may be provided to the user, so that the reference structure 120 is visualized.

For example, if the user wishes to visualize the real-time motion of a heart valve, the reference structure 120 may be the heart valve. By applying the model to arrive at a patient-specific segmentation, the position of the heart valve may be accurately determined. The determiner 370 may select an appropriate 2-D cross-section of the valve as the viewplane to be displayed. By repeatedly updating the imaging data and the patient-specific segmentation, the position of the heart-valve is followed and the representation on the screen is appropriately updated.

Typically, selection of the reference structure 120 will result in access to one or more criteria for the determiner 370 to determine the appropriate cross-section. Based upon generic or average anatomical data, for example, in case of the mitral valve, an optimal viewplane may be defined by the centers of gravity of the three valve leaflets. When the method is performed, a region of interest is determined based upon this average data and updated based upon the patient-specific anatomical data. Implementation of this may be further simplified by incorporating a set of anatomical landmarks in the anatomical model.

For systems combining visualization with functional measurements or therapeutic procedures, a suitable viewplane may be optimally determined based upon the target of the functional measurement or therapeutic procedure. For example, when the diameter of the left atrium or of the pulmonary vein ostia is being functionally measured, these structures may be used as the reference structure 120 for the visualization, and the viewplane may be determined and displayed.

A learning mode is also envisioned where the actions of earlier users are logged to establish a typical sequence of events for a particular procedure. These may then form the basis for the determination of the appropriate 2D cross-section by the determiner 370.

The skilled person will realize that the method of the invention may be modified to perform the invention, using a time-composite model comprising a series of time-shifted models. In that case, some kind of temporal marker, such as a relationship to the phase of the heartbeat, may simplify the synchronization with the images obtained during the measurement. In some cases, it may be acceptable to calculate a temporal average of the optimal viewplane for the time-composite model, and provide this to the determiner 370 to reduce the computational load.

Typically, the user input 350 is further configured to interact with the system, so that the user may influence and select what is displayed and how it is displayed, for example, sizes, colors.

As will be obvious to the skilled person, one or more of the visualization, therapeutic and functional measurement embodiments may be integrated into a single system either employing separate transducers or a single transducer that is switched between the required modes of operation.

Figure 3A:
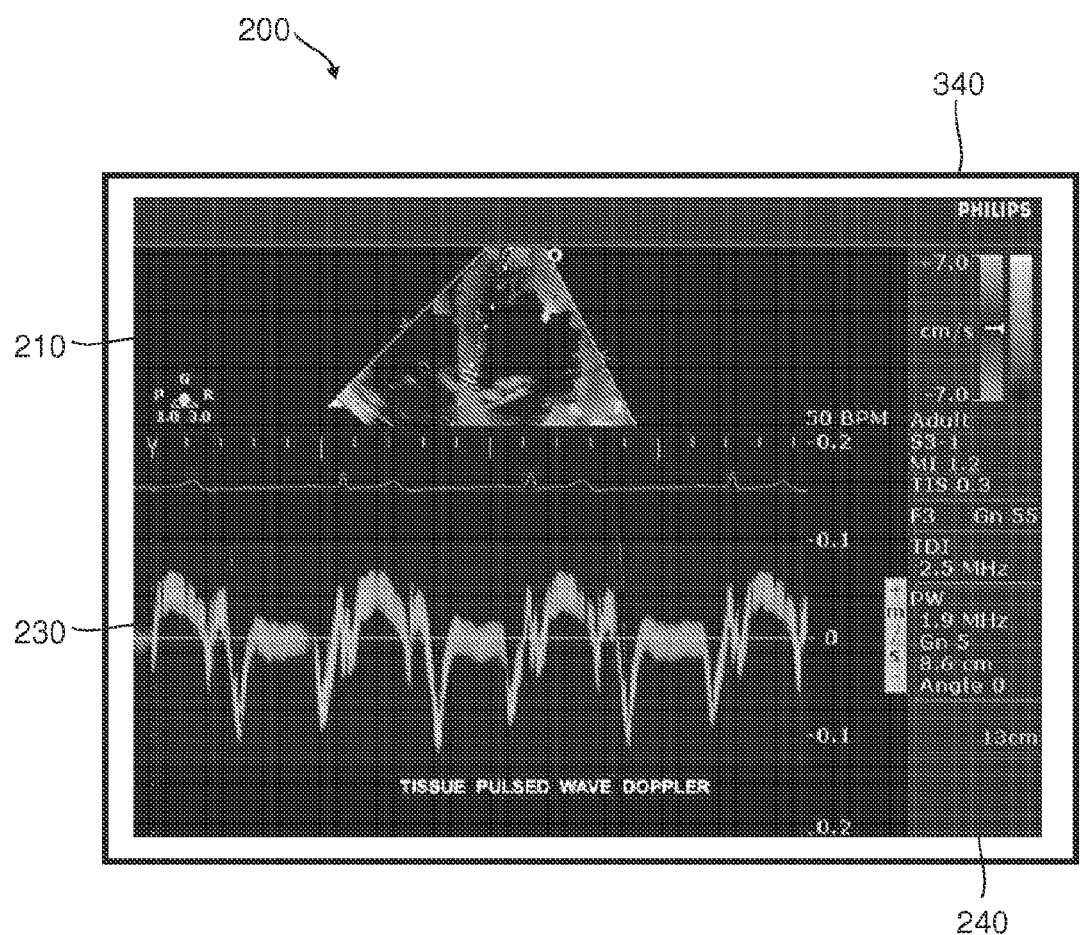
FIGS. 3A and 3B show examples of representations displayed to the user.

FIG. 3A shows an example of the display presented to the user by a system comprising a visualization embodiment and a functional embodiment based upon ultrasound imaging data.

Data representation 200 is displayed on a display 340 to the operator during a tissue pulsed wave Doppler measurement according to the invention. Details of pulsed Doppler measurement are well-known in the art.

Data representation 200 comprises elements derived from the visualization, and elements derived from the functional measurement. More specifically, there is provided a representation 210 of an anatomical volume, a functional representation 230 in the form of a velocity-time diagram, and a section 240 giving alphanumerical and symbolical information about scales, settings and the functional measurement results.

Figure 3B:
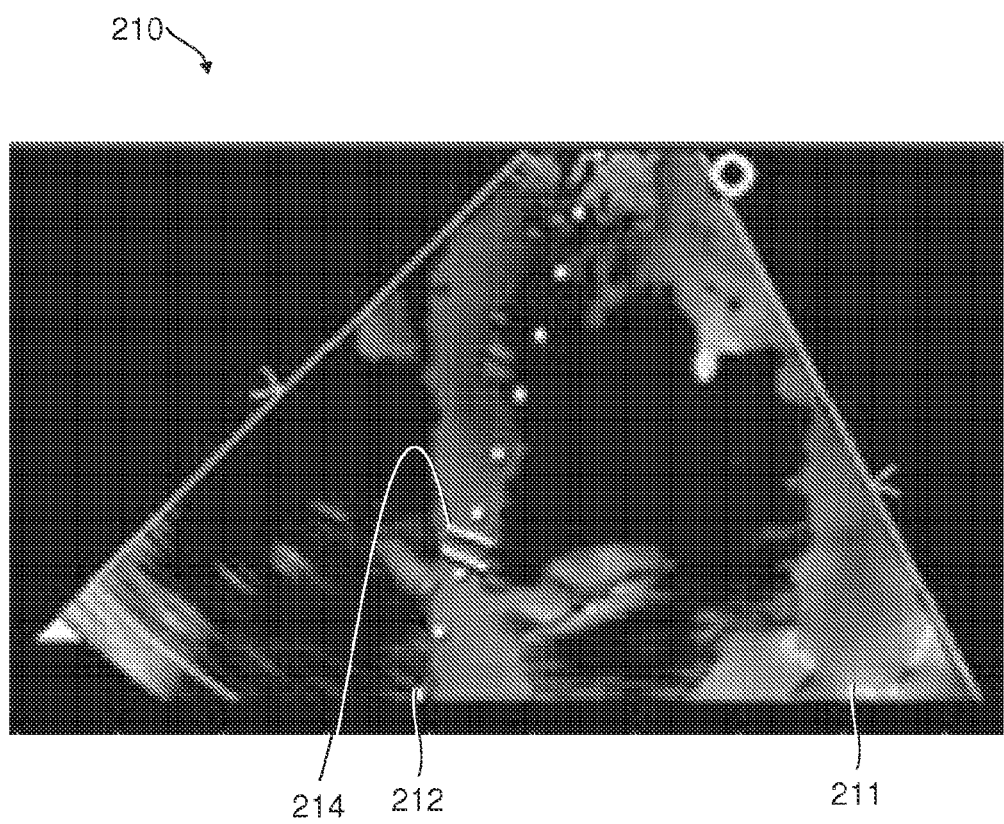

FIG. 3B depicts an enlargement of the representation 210 of FIG. 3A, comprising a background with the visualization of a 2D cross-section 211, overlaid with annotations derived from the functional measurement. The annotations comprise a line of measurement 212 and a target volume 214, the target volume 214 being disposed at a position along the measurement line 212, and oriented perpendicularly to the measurement line 212.

To produce the representation 200, the user places a suitable transducer 360 on the skin of a patient 110, adjacent to the blood vessel where the functional measurement is to be performed. The transducer 360 may be a single transducer 360 capable of being driven in a visualization and functional mode, such as B-mode and pulsed Doppler mode, respectively. Alternatively, two separate transducers may be used.

Using the visualization mode, imaging data of an anatomical volume 100 is acquired.

The user selects, using the user input 350, the desired section of the blood vessel as the reference structure 120 where the velocity measurement is to be performed. Alternatively, the blood volume within the section of the blood vessel may be selected as the reference structure 120.

Selection may be done by providing a 2D cross-section 211 on the display 340 acquired in the visualization mode, and allowing the user to select the section of the blood vessel by drawing a box around it. Alternatively, the user may select the section by clicking on it or using a drag and drop of a predetermined box.

The selection determines the model to be used for the segmentation, namely the model including the particular section of that particular blood vessel. The segmenter 330 applies the model to the imaging data from the visualization mode, thereby annotating the imaging data corresponding to the reference structure 120. Preferably, the small target volume 214 where the functional measurement is performed is then determined automatically by the determiner 370. It is assumed that the reference structure 120 is defined to comprise the small target volume 214.

Alternatively, the user may be required to select the small target volume 214, and the reference structure 120 is then determined automatically, or in a highly-automated system the user may be required to select both.

In some cases, the reference structure 120 may be the same as the target volume 214. However, in practice, the skilled person may implement them so as to be different, to adapt the system based upon the computational power available and the required skills of the user. In the latter case, the determiner 370 will then be further configured to convert between a reference structure 120 used for tracking purposes and the target volume 214 for measurement purposes, based upon their anatomical relationship.

The determiner 370 calculates functional data from the imaging data acquired during the functional measurement of the target volume 214, and provides the velocity-time diagram 230 on the display. Optionally, the target volume 214 may be overlaid onto the 2D cross-section 211 as an annotation. It may also be advantageous to overlay the line of measurement 212 onto the 2D cross-section 211.

By tracking the position of the reference structure 120, using the model-based segmentation, the anatomical position of the target volume 214 is correspondingly updated to optimize the accuracy of the functional measurement.

For the functional measurement, the orientation of the transducer 360 to the target volume 214 is used by the determiner 370 to determine the Doppler angle, and consequently to determine the velocity of the blood flow. The Doppler angle is the angle between the ultrasound beam 370 and the direction of blood flow in the target volume 214. Optionally, it may be advantageous to monitor the distance between the transducer 360 and the target volume 214 so that either the user can be alerted that the distance is outside a predetermined range, to automatically adjust the pulse repetition frequency based upon the distance, or to suggest to the user that the frequency should be changed.

A range of values for the distance may be provided to the determiner 370 in any way known in the art. The range may also be provided by incorporating reference values for this distance into the anatomical model.

Functional measurement results obtained may be ambiguous if additional anatomical structures are adjacent to the reference structure, such as (parallel) blood vessels near the target vessel. It may therefore be advantageous to extend the boundaries of the model used to encompass the reference structure 120 and its surrounding tissues, so that the positions of relevant adjacent structures are annotated. The determiner 370 may then be further configured to modify the region where the measurement is performed, or to correct the measurements for ambiguity.

The skilled person will be aware that geometric parameters may be derived from the segmented imaging data acquired in the visualization mode. The determiner may be further configured to determine geometric parameters corresponding to parameters derived during the functional measurement using the imaging data acquired in the functional mode. This may be advantageous to provide a check on the correctness of the measurements to reduce the risk of incorrect operation by the user.

The skilled person will also be aware that velocities and acceleration may also be determined from a time-shifted series of segmented imaging data. The determiner 370 may be further configured to calculate appropriate velocities and/or accelerations derived from the visualization mode, which may be compared to the velocities and/or accelerations calculated by the functional measurements. This may be used in pulsed Doppler measurement to alert the user to the problem of aliasing and therefore ambiguous results, to correct the aliasing problem by providing a reference velocity/acceleration, or to automatically update the pulse repetition frequency.

Information derived from the functional measurements may also be used to improve the model. For example, Doppler measurements may be used to check whether the measured direction of blood flow is consistent with the anatomical model, and if necessary, the system 300 may update the model.

Optionally, the model may be extended to comprise further information in addition to the geometric or anatomical information. For example, hemodynamic information about blood flow velocities, electro-mechanical information about electrically-triggered muscle contractions, electrical information about the spread of electricity in the tissues. It will be apparent to the skilled person that this additional information may be related to functional measurements. This additional information may therefore be used to provide initial settings for functional measurements, to provide predetermined values or ranges of values against which the functional measurements are compared for deviations, and even to allow the measurements made using the invention to be used to create or adapt such a functional model.

For example, actual blood flow velocity measurements using pulsed Doppler may be provided to improve the accuracy and prediction of a combined hemodynamic/anatomic model.

In a further embodiment of the invention, the system further comprises a tracker 335 configured to determine the position of a surgical instrument 130 in the anatomical volume 100, and the determiner 370 is further configured to determine a second vector between the reference structure 120 and the surgical instrument 130. For example, the instrument 120 may be a catheter, and the reference structure 120 may be the septum or the pulmonary veins.

Tracking of the surgical instrument 130, such as a catheter, may be provided using an appropriate instrument detector 365 for which the spatial orientation with respect to the transducer 360 is known, as depicted in FIGS. 1 and 4. Instrument trackers are well-known in the art, and any suitable system may be employed, such as catheter tracking algorithms.

Alternatively, the imaging data acquired by the transducer 360 may be segmented by the tracker 335 to locate the instrument 130. This is preferred as it reduces the complexity of the system.

The determiner 370 calculates the orientation of the instrument 130 with respect to the reference structure 120.

It may be advantageous to further configure the determiner 370 to monitor a geometric parameter associated with the instrument 130, and to alert the user if the geometric parameter deviates from a predetermined value or a range of values. Examples thereof include: the orientation of the instrument 130 with respect to the reference structure 120, possibly expressed as a vector, the proximity of the surgical instrument 130 to a boundary of the anatomical volume 100, the proportion of the surgical instrument 130 within the anatomical volume 100, or any combination thereof.

The parameter may even be a geometric quantity of the instrument 130, as geometry may be derivable from the patient-specific segmented data.

It may be advantageous to consider the position of the instrument when visualization cross-sections are determined. For example, the determiner 370 may be further configured to determine from the annotated data a viewing cross-section based upon the orientation of the transducer 360 and the instrument 130 relative to the reference structure, wherein the viewing cross-section intersects the reference structure 120 and the surgical instrument 130.

When using the systems and methods of the prior art, the operator would need to frequently change viewplanes manually if the instrument moved out of the current viewplane, or if the orientation was lost due to the small field of view represented on the display. By continuously tracking the position of the reference structure 120 and the instrument 130, their position within the anatomical volume 100 may be accurately and repeatedly determined, allowing an automatic or highly-automated selection of a new viewplane as the instrument 130 is moved towards the reference structure 120. Optionally, the user may be provided with coordinates of the reference structure 120 and the instrument 130, and the distance between them may also be determined and provided.

It is also envisioned that multiple representations be provided to the user, such as split-screens so that viewplanes are generated for both the reference structure 120 and the instrument 130. Such techniques reduce the possibility that the orientation of the instrument 130 relative to the reference structure 120 is lost.

It may be advantageous to record the various parameters and values during the procedures, such as the position of the determined viewplane for geometric or functional measurements. Such data may be used for comparison purposes.

The skilled person, provided with the details of the methods disclosed, will be able to implement a computer program to carry out these methods when loaded and run on a computer.

A user may use a workstation to perform these interactions, for example during image acquisition, image viewing, image analysis and image modification. The workstation may then comprise the system according to the invention. It is also envisioned that the system 300 may be comprised in a medical image acquisition apparatus.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer.

In the system claim enumerating a user input, an imager, a model input, a segmenter, a determiner, a tracker, and a display, several of these means may be embodied by one and the same item of hardware.

The mere fact that certain measures are recited in mutually different dependent claims does not indicate that a combination of these measures cannot be used to advantage.

The invention claimed is:

1. A system for repeated determination of a first vector between:
    a reference structure comprised in an anatomical volume, and
    a medical imaging transducer configured to provide imaging data of the anatomical volume;
    the system comprising:
        a user input configured to specify the reference structure;
        an imager configured to receive the imaging data;
        a model input configured to provide a model of the reference structure;

a segmenter configured to receive the model and to segment the imaging data, using the model, whereby the imaging data associated with the reference structure is at least partially annotated, and a determiner configured to receive the annotated imaging data of the reference structure and to determine the first vector between the transducer and the reference structure based on the annotated imaging data.

2. The system of claim 1, wherein:

the determiner is further configured to monitor a geometric parameter selected from the group consisting of:

the length of the first vector, the direction of the first vector, the proximity of the reference structure to a boundary of the anatomical volume, the proportion of the reference structure within the anatomical volume, a geometric quantity of the reference structure, or any combination thereof;

the determiner being further configured to alert the user if the geometric parameter deviates from a predetermined value or range of values.

3. The system of claim 1, wherein:

the determiner is further configured to determine from the annotated data a viewing cross-section based upon the first vector, wherein the viewing cross-section intersects the reference structure and the system further comprises:

a display configured to provide a representation of the viewing cross-section.

4. The system of claim 1, wherein:

the determiner is further configured to determine a functional parameter based upon the segmented data of the reference structure.

5. The system of claim 1, wherein the system further comprises:

a tracker configured to determine the position of a surgical instrument in the anatomical volume, and the determiner is further configured to determine a second vector between the reference structure and the surgical instrument.

6. The system of claim 5, wherein:

the determiner is further configured to monitor a geometric parameter selected from the group consisting of:

the length of the second vector, the direction of the second vector, the proximity of the surgical instrument to a boundary of the anatomical volume, the proportion of the surgical instrument within the anatomical volume, a geometric quantity of the instrument, or any combination thereof;

the determiner being further configured to alert the user if the geometric parameter deviates from a predetermined value or range of values.

7. The system of claim 5, wherein the tracker is comprised in the segmenter and further configured to segment the imaging data, whereby the imaging data associated with the surgical instrument is at least partially annotated.

8. The system of claim 5, wherein the system further comprises an instrument detector configured to detect the surgical instrument, and the tracker is configured to determine the position of the surgical instrument in the anatomical volume based upon signals from the instrument detector.

9. The system of claim 5, wherein:

the determiner is further configured to determine from the annotated data a viewing cross-section based upon the first and second vector, wherein the viewing cross-section intersects the reference structure and the surgical instrument, and the system further comprises:

a display configured to provide a representation of the viewing cross-section.

10. A workstation or a medical imaging acquisition apparatus comprising the system according to claim 1.

11. A method for repeated determination of a first vector between:

a reference structure comprised in an anatomical volume, and a medical imaging transducer configured to provide imaging data of the anatomical volume;

the method comprising:

a user specifying the reference structure;

providing a model of the reference structure;

segmenting the imaging data using the model, whereby the imaging data associated with the reference structure is at least partially annotated, and determining the first vector between the transducer and the reference structure based on the annotated imaging data of the reference structure.

12. The method of claim 11, the method further comprising:

monitoring a geometric parameter selected from the group consisting of:

the length of the first vector, the direction of the first vector, the proximity of the reference structure to a boundary of the anatomical volume, the proportion of the reference structure within the anatomical volume, a geometric quantity of the reference structure, or any combination thereof;

alerting the user if the geometric parameter deviates from a predetermined value or range of values.

13. The method of claim 11, wherein the method further comprises:

determining the position of a surgical instrument in the anatomical volume, and determining a second vector between the reference structure and the surgical instrument.

14. The method of claim 13, wherein the method further comprises:

monitoring a geometric parameter selected from the group consisting of:

the length of the second vector, the direction of the second vector, the proximity of the surgical instrument to a boundary of the anatomical volume, the proportion of the surgical instrument within the anatomical volume, a geometric quantity of the instrument, or any combination thereof;

alerting the user if the geometric parameter deviates from a predetermined value or range of values.

15. A non-transitory computer readable storage medium including a set of instructions executable by a processor, the set of instructions, when executed, cause the processor to perform operations comprising:

a user specifying a reference structure comprised in an anatomical volume;

providing a model of the reference structure;

segmenting the imaging data using the model, whereby the imaging data associated with the reference structure is at least partially annotated, and repeatedly determining a first vector between a medical imaging transducer configured to provide imaging data of the anatomical volume and the reference structure, wherein the determining is based on the annotated imaging data of the reference structure.

* * * * *